US009254325B2

(12) United States Patent
Kurita

(10) Patent No.: US 9,254,325 B2

(45) Date of Patent: Feb. 9, 2016

(54) PERCUTANEOUSLY ABSORBED PREPARATION

(75) Inventor: Hisakazu Kurita, Tsukuba (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 217 days.

(21) Appl. No.: 13/881,807

(22) PCT Filed: Oct. 26, 2011

(86) PCT No.: PCT/JP2011/074704

§ 371 (c)(1),
(2), (4) Date: Apr. 26, 2013

(87) PCT Pub. No.: WO2012/057220

PCT Pub. Date: May 3, 2012

(65) Prior Publication Data

US 2013/0211352 A1 Aug. 15, 2013

(30) Foreign Application Priority Data

Oct. 28, 2010 (JP) ................................ 2010-242253

(51) Int. Cl.

| | |
|---|---|
| ***A61K 47/12*** | (2006.01) |
| ***A61K 9/00*** | (2006.01) |
| ***A61K 9/06*** | (2006.01) |
| ***A61K 9/70*** | (2006.01) |
| ***A61K 31/4174*** | (2006.01) |
| ***A61K 47/18*** | (2006.01) |
| ***A61K 47/32*** | (2006.01) |
| ***A61K 47/34*** | (2006.01) |

(52) U.S. Cl.

CPC ............... *A61K 47/12* (2013.01); *A61K 9/0014* (2013.01); *A61K 9/0024* (2013.01); *A61K 9/06* (2013.01); *A61K 9/7061* (2013.01); *A61K 31/4174* (2013.01); *A61K 47/18* (2013.01); *A61K 47/32* (2013.01); *A61K 47/34* (2013.01)

(58) Field of Classification Search

CPC ....... A61K 9/004; A61K 9/06; A61K 9/7061; A61K 31/4174; A61K 47/34; A61K 47/32; A61K 47/12; A61K 9/0024; A61K 47/18

See application file for complete search history.

(56) References Cited

U.S. PATENT DOCUMENTS

| | | | | |
|---|---|---|---|---|
| 5,762,953 | A | 6/1998 | Venkateshwaran | |
| 6,117,864 | A | 9/2000 | Morita et al. | |
| 2005/0260255 | A1* | 11/2005 | Terahara et al. | .............. 424/449 |
| 2006/0188554 | A1 | 8/2006 | Nakashima et al. | |
| 2009/0123526 | A1 | 5/2009 | Kuribayashi | |
| 2009/0130180 | A1 | 5/2009 | Kajita et al. | |
| 2011/0071204 | A1 | 3/2011 | Takahashi et al. | |
| 2011/0152377 | A1 | 6/2011 | Hanma et al. | |
| 2012/0029446 | A1 | 2/2012 | Amano et al. | |

FOREIGN PATENT DOCUMENTS

| | | | |
|---|---|---|---|
| JP | 2009-242303 | A | 10/2009 |
| WO | WO 2005/011683 | A1 | 2/2005 |
| WO | WO 2006/082888 | A1 | 8/2006 |
| WO | WO 2006/093139 | A1 | 9/2006 |
| WO | WO 2007/023791 | A1 | 3/2007 |
| WO | WO 2010/016219 | A1 | 2/2010 |
| WO | WO 2010/095537 | A1 | 8/2010 |

* cited by examiner

*Primary Examiner* — Ali Soroush
*Assistant Examiner* — Genevieve S Alley
(74) *Attorney, Agent, or Firm* — Wolf, Greenfield & Sacks, P.C.

(57) ABSTRACT

The purpose of the invention is to produce an imidafenacin-containing percutaneously absorbed preparation, wherein the drug not only is not allowed to crystallize but also has adequate skin penetration. The imidafenacin-containing percutaneously absorbed preparation comprises isostearic acid and a fatty acid ester, which function as crystallization-preventing agents.

18 Claims, No Drawings

PERCUTANEOUSLY ABSORBED PREPARATION

RELATED APPLICATION

This application is a national stage filing under 35 U.S.C. §371 of international application PCT/JP2011/074704, filed Oct. 26, 2011, the disclosure of which is incorporated by reference herein in its entirety.

TECHNICAL FIELD

The present invention relates to a percutaneous absorption preparation comprising imidafenacin and/or a salt thereof and isostearic acid.

BACKGROUND ART

In order to obtain drug efficacy by administering a drug, an oral administration method is generally used; however, transdermal administration method has many advantages compared to oral administration method. For example, in oral administration method, a drug absorbed in the bowel is first metabolized in the liver so that a large amount of the drug is decomposed before it exhibits drug efficacy in desired regions; whereas in transdermal administration method, the absorbed drug does not pass initially through the liver in the body circulation, and therefore its efficacy is not significantly decreased in the liver due to metabolism. Furthermore, transdermal administration method has other advantages such as, at the drug effect is continuous, and it has a sustained drug release characteristics.

In addition, as an advantage of transdermal administration method, reduction of side effects can be expected by sustained release of drugs and by maintaining their constant blood levels in particular, there is a tendency that transdermal administration preparations that can be administered for a long period of time (1 day to 7 days) are desired from the viewpoint of patient compliance.

In such percutaneous absorption preparations, an important issue is how to effectively release the drug (medicinal ingredient) from a base, namely, to effectively transfer the drug from the base to the skin. In general, when formulation design is attempted using a specific drug, quite often crystallization, etc. occurs due to insufficient dissolution of the drug in a base, resulting in a decreased level of drug release and insufficient therapeutic effect. In addition, crystallization is undesirable from the viewpoint of long-term storage of preparations. Accordingly, selection of a crystallization inhibitor is important for percutaneous absorption preparations. Furthermore, because a drug is absorbed through the skin, it is necessary to increase the skin permeability of the drug. Therefore, selection of the optimal dissolving agent for the drug is important in the formulation design; depending on the selection of dissolving agent, dissolution of the drug becomes insufficient, leading to a decreased level of release of the drug from the base and decreased level of transfer of the drug to a diseased part, and consequently, sufficient therapeutic effect cannot be exerted.

Imidafenacin (4-(2-methyl-1H-imidazol-1-yl)-2,2-diphenylbutane amide) is a muscarinic receptor antagonist having a M3 and M1 muscarinic receptor antagonistic activity selective for the bladder, and is a therapeutic drug for urinary frequency and urinary incontinence.

While imidafenacin has been used as an agent for oral administration in the current clinical setting, from the viewpoints of reduction of side effects such as liver failure, stabilization of blood concentration for a long period of time, and long-sustaining effects, development of transdermal administration preparations such as adhesive patch, etc., rather than oral administration preparations, has been desired.

Based on such current situation, percutaneous absorption preparations comprising imidafenacin have been proposed (Patent Literatures 1 and 2).

In Patent Literatures 1 and 2, a percutaneous absorption preparation comprising 4-(2-methyl-1H-imidazol-1-yl)-2,2-diphenylbutane amide (imidafenacin) is described; however, since imidafenacin has low skin permeability, in order to use it in a skin-absorption type preparation wherein a drug is efficiently absorbed through the skin, it is necessary to increase its skin permeability and to suppress crystallization. However, in Patent Literatures 1 and 2, a means for solving such problems has not been provided.

In Patent Literature 3, an adhesive patch composed of a backing and an adhesive layer comprising a free-basic drug, an adhesive agent and a fatty acid having an aliphatic hydrocarbon group with a carbon number of 8-22; however, this does not provide a means for solving the problem of inhibiting the crystallization simultaneously without decreasing the skin permeability in percutaneous absorption preparations comprising imidafenacin as the therapeutic agent for urinary frequency and urinary incontinence.

CITATION LIST

Patent Literature

Patent Literature 1: WO 2005/011683
Patent Literature 2: WO 2006/082888
Patent Literature 3: JP, A, 2009/242303

SUMMARY OF INVENTION

Technical Problem

Therefore, the present inventors have obtained recognition that regarding percutaneous absorption preparations comprising imidafenacin, a skin-absorption type preparation having sufficient skin permeability of the drug without crystallization should be produced. Namely, the problem to be solved by the present invention is to provide a percutaneous absorption preparation that realizes stable absorption of imidafenacin through the skin and that has storage stability.

Solution to Problem

Through extensive research to solve the above problem, the present inventors have discovered that, in a percutaneous absorption preparation comprising imidafenacin, inhibition of crystallization and stable absorption of the drug through the skin can be realized by comprising isostearic acid that functions as a crystallization inhibitor as well as an fatty acid ester; and the present inventors have accomplished the present invention.

Namely, the present invention relates to the followings:

(a) A percutaneous absorption preparation comprising imidafenacin and/or a salt thereof, isostearic acid and a fatty acid ester.

(b) The percutaneous absorption preparation according to (a), wherein the isostearic acid is a crystallization inhibitor.

(c) The percutaneous absorption preparation according to (a) or (b), wherein the amount of isostearic acid contained in the percutaneous absorption preparation is 2-20 mass %.

(d) The percutaneous absorption preparation according to any one of (a) to (c), wherein the fatty acid ester is sorbitan monolaurate.

(e) The percutaneous absorption preparation according to any one of (a) to (d), further comprising triacetin as a percutaneous absorption promoting agent.

(f) The percutaneous absorption preparation according to any one of (a) to (e), wherein at 15 hr after its application, the skin permeation rate is greater than 2.0 $\mu g/cm^2/hr$, and the cumulative amount of permeation is greater than 30 $\mu g/cm^2$.

(g) The percutaneous absorption preparation according to any one of (a) to (f), which is a skin external patch comprising a pressure-sensitive adhesive composition that comprises a pressure-sensitive adhesive base.

(h) The percutaneous absorption preparation according to (g), comprising a (meth)acrylic acid ester copolymer as the pressure-sensitive adhesive base.

(i) The percutaneous absorption preparation according to (g) or (h), which is a skin external patch having a structure in which the pressure-sensitive adhesive composition is laminated on a backing and covered with a liner.

(j) A method for producing a percutaneous absorption preparation comprising imidafenacin and/or a salt thereof, wherein isostearic acid as a crystallization inhibitor and a fatty acid ester are further comprised.

Advantageous Effects of Invention

The percutaneous absorption preparation of the present invention, without crystallization of imidafenacin, has good skin permeability, and has storage stability and enables stable absorption of imidafenacin, so that it is extremely useful for the treatment of urinary frequency, urinary incontinence and others.

DESCRIPTION OF EMBODIMENTS

The percutaneous absorption preparation of the present invention is a percutaneous absorption preparation comprising imidafenacin and/or a salt thereof, isostearic acid that functions as a crystallization inhibitor, and a fatty acid ester.

The amount of imidafenacin and/or a salt thereof contained in the percutaneous absorption preparation of the present invention is not particularly limited, and is preferably 1-10 mass %, more preferably 1-5 mass %, and most preferably 1-3 mass %.

The amount of isostearic acid contained in the percutaneous absorption preparation of the present invention is not particularly limited, and is preferably 1-20 mass %, more preferably 2-7 mass %.

The amount of sorbitan monolaurate contained in the percutaneous absorption preparation of the present invention is not particularly limited, and is preferably 1-20 mass %, more preferably 3-10 mass %.

As a percutaneous absorption promoting agent that can be used in the percutaneous absorption preparation of the present invention, any compound that has conventionally been recognized to have an absorption promoting action in the skin may be used, and examples include, fatty acids having 6-20 carbon chains, fatty alcohols, fatty acid esters, fatty acid amides, fatty acid ethers, aromatic organic acids, aromatic alcohols, aromatic organic acid esters or ethers (the above may be either saturated, or unsaturated, and any of cycle straight-chain and branched chain), and furthermore, lactic acid esters, acetic acid esters, monoterpene compounds, sesquiterpene compounds, Azone, Azone derivatives, pyrothiodecane, glycerin fatty acid esters, propylene glycol fatty acid esters, sorbitan fatty acid esters, (Span series) polysorbates (Tween series), polyethylene glycol fatty acid esters, polyoxyethylene hardened castor oils type (HCO series), polyoxyetheyl alkyl ethers, sucrose fatty acid esters, and vegetable oils, etc.

Specifically, preferable examples include triacetin, caprylic acid, capric acid, caproic acid, lauric acid, myristic acid, palmitic acid, stearic acid, isostearic acid, oleic acid, linoleic acid, linolenic acid, lauryl alcohol, myristyl alcohol, oleyl alcohol, isostearyl alcohol, cetyl alcohol, octyldodecanol, stearyl alcohol, methyl laurate, hexyl laurate, diethyl sebacate, lauric acid diethanolamide, isopropyl myristate, myristyl myristate, octyldodecyl myristate, cetyl palmitate, salicylate, cinnamic acid, methyl salicylate, ethylene glycol salicylate, cinnamic acid, methyl cinnamate, cresol, cetyl lactate, lauryl lactate, ethyl acetate, propyl acetate, geraniol, thymol, eugenol, terpineol, l-menthol, borneol, d-limonene, isoeugenol, isoborneol, nerol, dl-camphor, glycerin monocaprylate, glycerin monocaprate, glycerin monolaurate, glycerin monooleate, sorbitan monolaurate, sucrose monolaurate, polysorbate 20, propylene glycol, propylene glycol monolaurate, polyethylene glycol monolaurate, polyethylene glycol monostearate, polyoxyethylene lauryl ether, HCO-60, pyrothiodecane, and olive oil; particularly preferable examples include lauryl alcohol, myristyl alcohol, oleyl alcohol, isostearyl alcohol, diethyl sebacate, diethanolamide laurate, isopropyl myristate, glycerin monocaprate, glycerin monolaurate, glycerin monooleate, sorbitan monolaurate, propylene glycol monolaurate, polyoxyethylene lauryl ether, and pyrothiodecane.

More preferable examples include triacetin, isopropyl myristate, oleyl alcohol, octyldodecanol and stearyl alcohol, and the most preferred is triacetin. A percutaneous absorption promoting agent can be appropriately selected depending on the intended use (dose regimen and dosage).

Two or more kinds or percutaneous absorption promoting agents may be mixed and co-used; with consideration given to sufficient permeability as a percutaneous absorption preparation and skin irritation such as redness and edema, etc., the percutaneous absorption promoting agents may be blended in an amount of 0.01-40 mass %, more preferably 0.05-30 mass %, and particularly preferably 0.1-20 mass %, based on the weight of the total composition of the percutaneous absorption preparation.

The amount of triacetin contained in the percutaneous absorption preparation of the present invention is not particularly limited, and is preferably 1-10 mass %, more preferably 3-8 mass %.

The amount of isopropyl myristate contained in the percutaneous absorption preparation of the present invention is not particularly limited, and is preferably 1-15 mass %, more preferably 3-10 mass %.

The amount of oleyl alcohol, octyldodecanol or stearyl alcohol, contained in the percutaneous absorption preparation of the present invention is not particularly limited, and is preferably 1-15 mass %, more preferably 3-10 mass %.

There is no particular limitation on the dosage form of the percutaneous absorption preparation of the present invention, and dosage forms conventionally used as a skin external preparation may be used; for example, any dosage forms including skin external patch, poultice, plaster, ointment, gels, creams, lotion, reservoir-type patch, liniment, aerosol and others may be used for the percutaneous absorption preparation.

The skin external patch has preferably a structure in which a pressure-sensitive adhesive composition is laminated on a backing and covered with a liner.

As a backing of skin external patch, the following materials with and without stretching properties are selected: for example, a film, a sheet or a foil of polyethylene, polypropylene, polybutadiene ethylene-vinyl acetate copolymer, polyvinyl chloride, polyesters such as polyethylene terephthalate (PET), polybutylene terephthalate, and polyethylene naphthalate, nylon, polyurethane, cotton, rayon (cellulose derivatives), and aluminum, etc., and a porous form and a foam thereof, as well as paper, woven fabric, knitted fabric, and nonwoven fabric etc., and laminates thereof can also be used.

As a liner of skin external patch, a film, a sheet, or a foil of polyethylene, polypropylene, polyesters such as polyethylene terephthalate (PET) and polyethylene naphthalate, nylon, aluminum, etc., or paper, etc. may be selected; and a laminate thereof may also be used. In addition, in order to facilitate peeling of the pressure-sensitive adhesive, the surface of said liner may be treated with silicon, Teflon®, a surfactant, etc.

Next, poultice and plaster will be explained. For example, as a base of poultice, with consideration given to stability, release characteristics, percutaneous absorption characteristics and safety for the skin, a hydrophilic base blending water-soluable polymer, polyhydric alcohol and water is used.

As the water-soluable polymer used in this hydrophilic base, one or more kinds are appropriately selected from the following: gelatin, casein, pullulan, dextran, sodium alginate, soluble starch, carboxymethyl starch, dextrin, carboxymethyl cellulose, carboxymethyl cellulose sodium, methyl cellulose, ethyl cellulose, hydroxyethyl cellulose, polyvinyl alcohol, polyethylene oxide, polyacrylic acid, polyacrylamide, sodium polyacrylate, polyvinyl pyrrolidone, carboxyvinyl polymer, polyvinyl ether, methoxy ethylene-maleic anhydride copolymer, isobutylene-maleic anhydride copolymer, N-vinyl acetamide, copolymer of N-vinyl acetamide and acrylic acid and/or acrylate. In this case, the amount of water-soluble polymer blended is 1-30 mass %, preferably 1-20 mass %, and more preferably 1-30 mass % relative to the total amount of the preparation. When the amount of blending is too small, viscosity decreases and the degree of shape retention decreases; when the amount of blending is too large, viscosity increases and workability during kneading and coating decreases.

As the polyhydric alcohol, one kind, or two or more kinds as necessary, are appropriately selected from the following: polyethylene glycol, propylene glycol, dipropylene glycol, polypropylene gylcol, 1,3-butylene glycol, 1,4-butylene glycol, isobutylene glycol, glycerin diglycerin, sorbitol, etc.; and its amount of blending is 10-90 mass %, preferably 10-70 mass %, and more preferably 20-60 mass %. When the amount of blending is too small, moisture-retaining effect decreases; when it is too large, solubility of water-soluble polymer is affected. The amount of water blended is 10-90 mass %, preferably 20-80 mass %; water is necessary to dissolve water-soluble polymers and to exhibit their viscosity, cohesiveness and shape retention characteristic.

Furthermore, in addition the above essential components, one or more or agents may be appropriately blended as necessary, and examples of the crosslinking agents include polyvalent metal compounds, specifically, aluminum hydroxide, aluminum chloride, calcium hydroxide, calcium chloride, aluminum sulfate, aluminum ammonium sulfate, aluminum potassium sulfate, magnesium aluminometasilicate, dihydroxy aluminum aminoacetate, etc.; other examples of the crosslinking agents include compounds having at least two epoxy groups in the molecule, specifically, ethylene glycol diglycidyl ether, polyethylene glycol diglycidyl ether, propylene glycol diglycidyl ether, polypropylene glycol diglycidyl ether, polytetramethylene glycol diglycidyl ether, glycerol polyglycidyl ether, polyglycerol polyglycidyl ether, sorbitol polyglycidyl ether, sorbitan polyglycidyl ether, trimethylolpropane polyglycidyl ether, pentaerythritol polyglycidyl ether, resorcinol diglycidyl ether, neopentyl glycol diglycidyl ether, 1,6-hexanediol diglycidyl ether, etc.

In addition, one or more components consisting of a filler such as kaolin, zinc oxide, titanium dioxide, talc, bentonite, synthetic aluminum silicate, etc., a preservative such as thymol, methyl paraben, ethyl paraben, etc., an antioxidant such as ascorbic acid, stearic acid ester, dibutyl hydroxy toluene, butyl hydroxy anisole, gallic acid ester, vitamin E, vitamin E acetate, disodium edetate, etc., a UV absorber such as 2-hydroxy-4-methoxybenzophenone, ethyl p-aminobenzoate, 2-(2-hydroxy-5-methylphenyl) benzotriazole, glycol salicylate, methyl salicylate, phenyl salicylate, etc., and an emulsifying agent such as sorbitan fatty acid ester, glycerin fatty acid ester, decaglycerol fatty acid ester, polyoxyethylene sorbitan fatty acid ester, polyethylene glycol fatty acid ester, polyoxyethylene alkyl ether, etc. may be appropriately blended.

As a backing of this poultice, it is important to select a material that does not affect the release of medicinal ingredients. Namely, a backing having no interaction with and no adsorption of medicinal ingredients is important. For example, a backing is selected from a film or a sheet of polyethylene, polypropylene, polyvinyl chloride, polyester, nylon, polyurethane, etc., or a porous form and a foam thereof, as well as fabric and nonwoven fabric; or it may be selected from a laminate of the film or sheet with the porous body, foamed body, fabric, or nonwoven fabric. Furthermore, as a covered material for peeling, polyethylene, polypropylene, polyester, or these materials mold-release-treated with silicone, as well as release paper, etc. may be used.

Next, methods for producing these poultices will be described; poultices are what can be easily produced by an already known method for producing. For example, a water-soluble polymer is mixed into polyhydric alcohol and water, dispersed and dissolved to make a homogenous kneaded mixture, to which a stabilizer, an antioxidant, an UV absorber, an emulsifier, a preservative, and an antibacterial agent are added as necessary. Then, medicinal ingredients are added, homogeneously dispersed, and the resulting mixture is directly spread on a backing; or it is once spread on a paper or film that has been mold-release-treated, then pressure-transferred onto the backing used. Here, the sequence of blending each base, medicinal ingredients as well as other components in the above production method is described only as an example, and the blending sequence is not limited thereto.

Next, regarding the plaster, its pressure-sensitive adhesive base may be appropriately selected from those known in the art in consideration of safety for the skin, release characteristics of medicinal ingredients, and adhesiveness to the skin, etc. Preferred pressure-sensitive adhesive includes acrylic type pressure-sensitive adhesive, rubber type pressure-sensitive adhesive, silicone type pressure-sensitive adhesive, etc.

The acrylic pressure-sensitive adhesive is not particularly limited as long as it is a copolymer comprising at least one (meth)acrylic acid derivative represented by 2-ethylhexyl acrylate, methyl acrylate, butyl acrylate, hydroxyethyl acrylate, 2-ethylhexyl methacrylate, etc. Examples that can be used include pressure-sensitive adhesives listed in "2007 Encyclopedia of Pharmaceutical Excipients" (edited by Japan Pharmaceutical Excipients Council), such as acrylic acid-acrylic acid octyl ester copolymer, 2-ethylhexyl acrylate/vinylpyrrolidone copolymer solution, acrylic acid ester-vinyl acetate copolymer, 2-ethylhexyl acrylate/2-ethylhexyl methacrylate/dodecyl methacrylate copolymer, meth acrylate/2-ethylhexyl acrylate copolymer resin emulsion, and acrylic polymers contained in an acrylic resin alkanolamine solution, as well as Eudragit, etc. (Higuchi Shokai Co., Ltd.), DURO-TAK acrylic pressure-sensitive adhesive series (from Henkel). In particular, acrylic pressure-sensitive adhesives having a hydroxyl group can be preferably used from the viewpoint of drug release characteristics.

Examples of the rubber pressure-sensitive adhesive include natural rubber, polyisoprene rubber, polyisobutylene, polyvinyl ether, polyurethane polyisoprene, polybutadiene, styrene-butadiene copolymer, styrene-isoprene copolymer, styrene-isoprene-styrene block copolymer, etc. As the silicone pressure-sensitive adhesive, those comprising polyorganosiloxane and polydimethyl siloxane as main ingredients are used.

As tackifiers which can be used in this setting, rosin types such as rosin, and hydrogenated, disproportionated, polymerized, and esterified rosin derivatives; terpene resin such as α-pinene; β-pinene, etc.; terpene-phenol resin, fatty acid, aromatic-, alicyclic copolymerized-petroleum resins, as well as alkyl-phenyl resin, xylene resin, etc. can be exemplified.

A softening agent an agent that plasticizes and softens base polymers to retain their adequate adhesion to the skin. Examples of such softening agent include polybutene, polyisobutylene, liquid paraffin, higher fatty acid esters such as isopropyl myristate, etc., and silicon oil, vegetable oils such as almond oil, olive oil, camellia oil, persic oil, and peanut oil.

As a backing of plaster, those which do not affect the release of medicinal ingredients are preferred, and those having stretching properties or non-stretching properties are used. For example, the backing is selected from a film or a sheet made from synthetic resins such as polyethylene, polypropylene, polybutadiene, ethylene-vinyl acetate copolymer, polyvinyl chloride, polyester, nylon, polyurethane, etc., and a laminate, a porous film, and a foam thereof, as well as paper, fabric and non-woven fabric, etc.

This plaster can be easily produced by a conventional known method for producing; for example, in the case of synthetic rubber tape, a pressure-sensitive adhesive base, a softening agent and a tackifier are mixed by heating at 120-160° C. using a mixing machine such as kneader or mixer, etc., and a medicinal ingredient is added to the mixture, then the mixture is directly spread on a polypropylene or polyester film, etc.; alternatively, the mixture is once spread on a sheet or film that has been mold-release-treated, which then covers a desired backing and is pressure-transferred on the backing.

In the case of plasters that use an acrylic pressure-sensitive adhesive, a pressure-sensitive adhesive base, a medicinal ingredient and an absorption promoting agent, and an additive as necessary are dissolved or dispersed in an appropriate solvent, and the resulting solution or fluid dispersion is directly applied on the surface or a backing, dried, to form typically an adhesive layer with a thickness of 30-200 μm. Alternatively, this solution or dispersion may be applied on a protective releasing paper, then the resulting adhesive layer obtained after drying may be attached to a backing. The solvent used in this method of producing, which is not particularly limited as long as it is an organic solvent having compatibility with all the blending components such as pressure-sensitive adhesive base and medicinal ingredients, etc., includes aromatic hydrocarbons such as toluene, benzene and xylene, etc., esters such as ethyl acetate, etc., halogenated hydrocarbons such as carbon tetrachloride, chloroform and methylene chloride, etc.

The base polymer of this plaster can be appropriately selected from those known in the art in consideration of safety for the skin, release characteristics of medicinal ingredients and adhesion to the skin, etc.; styrene-isoprene-styrene block copolymer having extremely low polarity is preferred. In addition, while a styrene-isoprene-styrene block copolymer is preferably exemplified above as a base polymer, it may be co-used with other polymers, such as polyisobutylene, etc.

A softening agent plasticizes and softens styrene-isoprene-styrene block copolymer, i.e., a base polymer, to maintain its adequate adhesiveness to the skin. As the softening agent, almond oil, olive oil, camellia oil, persic oil, peanut oil, paraffin, etc. are used. Its blending ratio is preferably 150-350 parts by weigh relative to 100 parts by weight of the styrene-isoprene-styrene block copolymer, from the viewpoint of ensuring sufficient level of viscosity.

Next, the blending recipe for other types of percutaneous absorption preparations, such as ointment, gels, creams, gelled creams, lotion, reservoir-type patch, liniment, and aerosol is briefly explained.

An ointment comprises, in addition to medicinal ingredients, at least a higher fatty acid such as myristic acid or ester thereof, waxes such as spermaceti, etc., surfactant such as polyoxyethylene, and hydrocarbons such as hydrophilic petrolatum, etc.

In the formulation of this ointment, for example, 5-15 mass % of a higher fatty acid or an ester thereof, 1-10 mass % of a surfactant, and 0.5-10 mass % of a medicinal ingredient are mixed at room temperature or under heating, then 4-10 mass % of a wax and 50-90 mass % of a hydrocarbon are added and either heated or melted by heating, kept at 50-100° C.; after all the components become a clear solution, it is homogeneously mixed by a homomixer. Then, it is cooled to room temperature with stirring to obtain an ointment.

Gels comprise, in addition to medicinal ingredients, at least a lower alcohol such as ethanol, water, a gelling agent such as carboxyvinyl polymer, and a neutralizing agent such as triethanolamine, etc.

In the formulation of the gels, for example, 0.5-5 mass % of a gelling agent is added to 55 mass % or less of water and allowed to swell. Meanwhile, 0.5-10 mass % of a medicinal ingredient is dissolved in a mixture of 40 mass % or less of a glycol with 60 mass % or less of a lower alcohol. These two mixtures are mixed, to which a neutralizing agent is added to adjust the pH to 4-7, and the gels are obtained.

Creams comprise, in addition to medicinal ingredients, at least a higher fatty acid ester such as myristic acid ester, water, hydrocarbons such as liquid paraffin, an emulsifying agent such as polyoxyethylene alkyl ether.

In the formulation of the creams, they are obtained by adding appropriate amounts of the above medicinal ingredient, higher fatty acid ester, hydrocarbon, and emulsifying agent, and by mixing and stirring the mixture.

Gel-cream has properties intermediate between gels and creams; it is obtained by blending, in addition to the above each component of the creams, a gelling agent such as carboxyvinyl polymer, etc., and a neutralizing agent such as diisopropanolamine, then by adjusting the pH to 4-8, preferably 5-6.5.

In the formulation of this gel-cream, for example, 0.5-10 mass % of a medicinal ingredient is dissolved in a mixture of 25 mass % or less of a higher fatty acid ester and 40 mass % or less of a lower alcohol, to which 5 mass % or less of an emulsifying agent is added. Meanwhile, 0.5-5 mass % of a gelling agent is added to water and allowed to swell. Then, these two mixtures are mixed using a homomixer and homogeneously emulsified, after which a neutralizing agent is added to adjust the pH to 4-8.

A lotion comprises, in addition to medicinal ingredients, at least a lower alcohol such as ethanol, etc., water and/or glycols.

In the formulation of this lotion, it is obtained by adding appropriate amounts of the above medicinal ingredient, lower alcohol, water and/or glycols, and by mixing and stirring them.

A reservoir-type patch is composed at least of (1) a backing layer, (2) a drug reservoir layer, (3) a drug release layer, and (4) a pressure-sensitive adhesive layer, wherein said (2) drug reservoir layer is composed of, in addition to medicinal ingredients, a base that comprises either (a) at least glycols, lower alcohol, water-soluble polymer, (b) at least alphatic alcohol and polyhydric alcohol, or (c) at least paraffin and silicone.

A liniment comprises, in addition to medicinal ingredients, at least an alcohol such as ethanol and polyethylene glycol, water, a fatty acid ester such as adipic acid and sebacic acid.

In the formulation of the liniment, it is obtained by mixing and stirring 0.5-10 mass % of a medicinal ingredient with 10-70 mass % of an alcohol, 55 mass % or less of water, and 60 mass % less of a fatty ester.

An aerosol comprises, in addition to medicinal ingredients, at least a lower alcohol, water, dimethyl ether and/or liquified petroleum gas; and medicinal adjuvants such as camphor, α-tocopherol, menthol, etc., may be blended as desired.

In the specific formulation of the aerosol, 0.5-10 mass % of a medicinal ingredient is blended with lower alcohol and water, filled Into an aerosol container, to which dimethyl ether and/or liquefied petroleum gas as a propellant are pressure-injected; and the aerosol is obtained.

Within the range that does not impair the object of the present various pharmaceutically acceptable additives, such as stabilizers, antioxidants, perfumes, fillers, UV absorbers, preservatives, antimicrobial agents, and other percutaneous absorption promoting agents can be added.

Examples

Hereinafter, the present invention is described in further detail with reference to examples; however, the present invention is not limited to these examples. Unless stated otherwise, "%" represents "mass %".

[Evaluation of Skin Permeability/Crystallization of Percutaneous Absorption Preparations]

Imidafenacin, isostearic acid, sorbitan monolaurate, and triacetin were comprised in an OH-group-containing acrylic pressure-sensitive adhesive base so as to achieve the blending ratios described in Table 1, and percutaneous absorption preparations were prepared. Permeability of each of the percutaneous absorption preparations through the skin of a hairless mouse was measured as follows.

On the side of the stratum corneum of the skin (at the lateral side of the body) removed from a hairless mouse, the above percutaneous absorption preparation was adhered, i.e., the above percutaneous absorption preparation was applied, and the skin was mounted on a flow-through type diffusion cell with the dermis side placed at the receptor phase side. At the receptor phase, phosphate buffered saline of pH 7.4 was circulated to maintain the skin surface temperature at 32±1° C., and samples were collected at regular intervals, drug concentrations were measured by high performance liquid chromatography, and skin permeation rates (Flux (μg/cm$^2$/hr)) were calculated.

As a result of such verification, crystallization was not observed in the percutaneous absorption preparations comprising isostearic acid, and therefore, they were demonstrated to be a percutaneous absorption preparation having good stability.

Furthermore, with the percutaneous absorption preparations comprising sorbitan monolaurate and/or triacetin in addition to the isostearic acid, not only that the crystallization was not observed, but also that a high skin permeation rate of greater than 2.0 μg/cm$^2$/hr was measured at 15 hr after the application; furthermore, a high $J_{max}$ value could be obtained in a short time ($T_{max}$), showing good permeation through the skin of a hairless mouse with a large cumulative amount of permeation exceeding 30 μg/cm$^2$. Thus, they were demonstrated to be a percutaneous absorption preparation having sufficient skin permeability in addition to preparation stability.

INDUSTRIAL APPLICABILITY

As described above, by means of comprising imidafenacin and/or a salt thereof, isostearic acid that functions as a crystallization inhibitor, and a fatty acid ester, the percutaneous absorption preparation of the present invention can be used as a skin-absorption type preparation having sufficient skin permeability, in addition to enabling inhibition of crystallization

TABLE 1

| | | Imidafenacin mass % | Isostearic acid mass % | Sorbitan monolaurate mass % | Triacetin mass % | Skin permeability in hairless mouse: $J_{max}$ μg/cm$^2$/hr | $T_{max}$ hr | Cumulative amount of permeation μg/cm$^2$ | Crystallization |
|---|---|---|---|---|---|---|---|---|---|
| Com. | Ex. 1 | 1 | — | — | — | 0.31 | 38 | 2.0 | Yes |
| Ex. | Ex. 2 | 1.5 | — | 5 | — | 2.22 | 21 | 35.8 | Yes |
| | Ex. 3 | 3 | — | — | 5 | 1.04 | 38 | 5.4 | Yes |
| | Ex. 4 | 1.5 | — | 5 | 5 | 3.53 | 15 | 53.5 | Yes |
| | Ex. 5 | 1.5 | — | 5 | 10 | 4.30 | 15 | 68.2 | Yes |
| Ex. | Ex. 6 | 1.5 | 10 | — | — | 1.08 | 45< | 6.7 | No |
| | Ex. 7 | 1.5 | 3 | 5 | — | 2.62 | 27 | 35.0 | No |
| | Ex. 8 | 1.5 | 3 | 5 | 5 | 3.20 | 15 | 52.0 | No |
| | Ex. 9 | 1.3 | 3 | 5 | 7 | 2.86 | 15 | 45.7 | No |
| | Ex. 10 | 1.5 | 4 | 5 | 7 | 3.23 | 15 | 51.6 | No |
| | Ex. 11 | 1.5 | 6 | 5 | 7 | 2.78 | 15 | 43.2 | No |

($J_{max}$: Maximum skin permeation rate, $T_{max}$: Time to reach the maximum skin permeation rate)

of imidafenacin; and therefore, the preparation is extremely useful for the treatment of urinary frequency and urinary incontinence.

The invention claimed is:

1. A percutaneous absorption preparation which is a skin external patch comprising a pressure-sensitive adhesive composition that comprises a pressure-sensitive adhesive base, the pressure sensitive adhesive composition comprising:

imidafenacin and/or a salt thereof at 1-10 mass % based on the total amount of the pressure sensitive adhesive composition;

isostearic acid at 2-20 mass % based on the total amount of the pressure sensitive adhesive composition; and sorbitan monolaurate as a fatty acid ester at 3-10 mass % based on the total amount of the pressure sensitive adhesive composition, wherein the pressure-sensitive adhesive base comprises an OH-group-containing acrylic pressure-sensitive adhesive base.

2. The percutaneous absorption preparation according to claim 1, wherein the isostearic acid is a crystallization inhibitor.

3. The percutaneous absorption preparation according to claim 1, the pressure sensitive adhesive composition comprising isostearic acid at 2-7 mass % based on the total amount of the pressure sensitive adhesive composition.

4. The percutaneous absorption preparation according to claim 1, the pressure sensitive adhesive composition comprising triacetin as a percutaneous absorption promoting agent at 0.1-20 mass % based on the total amount of the pressure sensitive adhesive composition.

5. The percutaneous absorption preparation according to claim 4, containing triacetin as a percutaneous absorption promoting agent at 3-8 mass % based on the total amount of the pressure sensitive adhesive composition.

6. The percutaneous absorption preparation according to claim 1, wherein at 15 hr after its application, the skin permeation rate is greater than 2.0 μg/cm$^2$/hr, and the cumulative amount of permeation is greater than 30 μg/cm$^2$.

7. The percutaneous absorption preparation according to claim 1, wherein the pressure-sensitive adhesive base consists of an OH-group-containing acrylic pressure-sensitive adhesive base.

8. The percutaneous absorption preparation according to claim 1, in which the pressure-sensitive adhesive composition is laminated on a backing and covered with a liner.

9. The percutaneous absorption preparation according to claim 1, containing imidafenacin and/or a salt thereof at 1-3 mass % based on the total amount of the pressure sensitive adhesive composition.

10. The percutaneous absorption preparation according to claim 1, the pressure sensitive adhesive composition comprising imidafenacin and/or a salt thereof at 1-3 mass % based on the total amount of the pressure sensitive adhesive composition, and isostearic acid at 2-7 mass % based on the total amount of the pressure sensitive adhesive composition.

11. The percutaneous absorption preparation according to claim 1, the pressure sensitive adhesive composition comprising imidafenacin and/or a salt thereof at 1-3 mass % based on the total amount of the pressure sensitive adhesive composition, isostearic acid at 2-7 mass % based on the total amount of the pressure sensitive adhesive composition, and triacetin as a percutaneous absorption promoting agent at 3-8 mass % based on the total amount of the pressure sensitive adhesive composition.

12. The percutaneous absorption preparation according to claim 1, the pressure sensitive adhesive composition comprising imidafenacin and/or a salt thereof at 1-3 mass % based on the total amount of the pressure sensitive adhesive composition, and isostearic acid at 2-7 mass % based on the total amount of the pressure sensitive adhesive composition, wherein the pressure sensitive adhesive base consists of an OH-group-containing acrylic pressure-sensitive adhesive base.

13. The percutaneous absorption preparation according to claim 1, the pressure sensitive adhesive composition comprising imidafenacin and/or a salt thereof at 1-3 mass % based on the total amount of the pressure sensitive adhesive composition, isostearic acid at 2-7 mass % based on the total amount of the pressure sensitive adhesive composition, and triacetin as a percutaneous absorption promoting agent at 3-8 mass % based on the total amount of the pressure sensitive adhesive composition, wherein the pressure sensitive adhesive base consists of an OH-group-containing acrylic pressure-sensitive adhesive base.

14. A method for producing a percutaneous absorption preparation according to claim 1, comprising the step of adding isostearic acid as a crystallization inhibitor and sorbitan monolaurate as a fatty acid ester to the pressure sensitive adhesive composition containing imidafenacin and/or a salt thereof.

15. The method according to claim 14, the pressure sensitive adhesive composition comprising imidafenacin and/or a salt thereof at 1-3 mass % based on the total amount of the pressure sensitive adhesive composition, and isostearic acid at 2-7 mass % based on the total amount of the pressure sensitive adhesive composition.

16. The method according to claim 14, the pressure sensitive adhesive composition comprising imidafenacin and/or a salt thereof at 1-3 mass % based on the total amount of the pressure sensitive adhesive composition, isostearic acid at 2-7 mass % based on the total amount of the pressure sensitive adhesive composition, and triacetin as a percutaneous absorption promoting agent at 3-8 mass % based on the total amount of the pressure sensitive adhesive composition.

17. The method according to claim 14, the pressure sensitive adhesive composition comprising imidafenacin and/or a salt thereof at 1-3 mass % based on the total amount of the pressure sensitive adhesive composition, and isostearic acid at 2-7 mass % based on the total amount of the pressure sensitive adhesive composition, wherein the pressure sensitive adhesive base consists of an OH-group-containing acrylic pressure-sensitive adhesive base.

18. The method according to claim 14, the pressure sensitive adhesive composition comprising imidafenacin and/or a salt thereof at 1-3 mass % based on the total amount of the pressure sensitive adhesive composition, isostearic acid at 2-7 mass % based on the total amount of the pressure sensitive adhesive composition, and triacetin as a percutaneous absorption promoting agent at 3-8 mass % based on the total amount of the pressure sensitive adhesive composition, wherein the pressure sensitive adhesive base consists of an OH-group-containing acrylic pressure-sensitive adhesive base.

* * * * *